United States Patent
Habeck et al.

[11] Patent Number: 6,093,385
[45] Date of Patent: Jul. 25, 2000

[54] 4,4-DIARYLBUTADIENES AS WATER-SOLUBLE PHOTOSTABLE UV FILTERS FOR COSMETIC AND PHARMACEUTICAL PREPARATIONS

[75] Inventors: Thorsten Habeck, Meckenheim; Horst Westenfelder, Neustadt; Thomas Wünsch, Speyer, all of Germany

[73] Assignee: BASF Aktiengesellschaft, Ludwigshafen, Germany

[21] Appl. No.: 09/336,733

[22] Filed: Jun. 21, 1999

[30] Foreign Application Priority Data

Jun. 26, 1998 [DE] Germany ............... 198 28 463

[51] Int. Cl.[7] ............... A61K 7/42; A61K 7/44; A61K 7/00
[52] U.S. Cl. ............... 424/59; 424/60; 424/400; 424/401
[58] Field of Search ............... 424/59, 60, 400, 424/401

[56] References Cited

U.S. PATENT DOCUMENTS

| | | | |
|---|---|---|---|
| 4,387,089 | 6/1983 | Depolo | 424/59 |
| 4,788,206 | 11/1988 | Guthrie et al. | 514/346 |
| 4,950,467 | 8/1990 | Phalangas et al. | 424/59 |
| 5,576,354 | 11/1996 | Deflandre et al. | 514/685 |
| 5,587,150 | 12/1996 | Deflandre et al. | 424/59 |

FOREIGN PATENT DOCUMENTS

| | | |
|---|---|---|
| 251398 | 1/1988 | European Pat. Off. . |
| 514491 | 11/1992 | European Pat. Off. . |
| 2440933 | 6/1980 | France . |

*Primary Examiner*—Shelley A. Dodson
*Attorney, Agent, or Firm*—Keil & Weinkauf

[57] ABSTRACT

Use of 4,4-diarylbutadienes of the formula I,

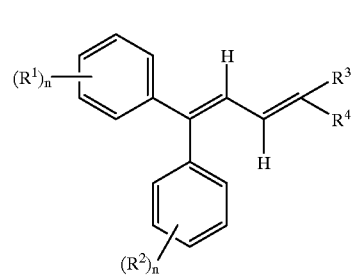

where the variables have the meanings explained in the description, as water-soluble photostable UV filters in cosmetic and pharmaceutical preparations for protecting the human skin or human hair from the sun's rays, alone or together with compounds which absorb in the UV region and are known per se for cosmetic and pharmaceutical preparations.

4 Claims, No Drawings

4,4-DIARYLBUTADIENES AS WATER-SOLUBLE PHOTOSTABLE UV FILTERS FOR COSMETIC AND PHARMACEUTICAL PREPARATIONS

The invention relates to the use of 4,4-diarylbutadienes as water-soluble photostable UV filters in cosmetic and pharmaceutical preparations for protecting the human epidermis or human hair from UV radiation, specifically in the range from 320 to 400 nm The sunscreens employed in cosmetic and pharmaceutical preparations have the task of preventing, or at least diminishing the consequences of, harmful effects of sunlight on the human skin. However, these sunscreens also serve to protect other ingredients from decomposition or breakdown by UV radiation. In hair cosmetic formulations the aim is to reduce damage to the keratin fibers by UV rays.

The sunlight reaching the surface of the earth contains UV-B radiation (280 to 320 nm) and UV-A radiation (>320 nm), which are directly adjacent to the visible light region. The effect on the human skin is manifested, particularly in the case of UV-B radiation, by sunburn. Accordingly, the industry offers a relatively large number of substances which absorb UV-B radiation and thus prevent sunburn.

Dermatoglogical investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancer in regions where the sun's radiation is strong shows that damage to the genetic information in the cells is evidently also caused by sunlight, specifically by UV-A radiation. All these findings therefore make it appear necessary to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the required effect by using the minimum amount, sunscreens of this type ought additionally to have a high specific extinction. Sunscreens for certain cosmetic products must also meet a large number of other requirements, for example good solubility in water or in water-miscible solvents, such as alcohols, high stability of the solutions or emulsions produced with them, toxicological acceptability, and slight intrinsic odor and slight intrinsic color.

Another requirement which sunscreens must meet is adequate photostability. However, this is only inadequately ensured, if at all, with the UV-A-absorbing sunscreens hitherto available.

French Patent No. 2 440 933 describes 4-(1,1-dimethylethyl)-4'-methoxydibenzoylmethane as a UV-A filter. It is proposed to combine this specific UV-A filter, which is sold by GIVAUDAN under the name "PARSOL 1789", with various UV-B filters in order to absorb all UV rays having a wavelength from 280 to 380 nm.

However, this UV-A filter does not have sufficient photochemical stability, when used alone or in combination with UV-B filters, to ensure sustained protection of the skin during sunbathing for prolonged periods, which means that repeated applications at regular and short intervals are required if effective protection of the skin from all UV rays is desired.

For this reason, EP-A-0 514 491 discloses the stabilization of the insufficiently photostable UV-A filters by adding 2-cyano-3,3-diphenylacrylic esters which themselves act as filters in the UV-B region.

It has furthermore already been proposed in EP-A-0 251 398 to combine chromophores absorbing UV-A radiation and UV-B radiation into one molecule by using a linker. This has the disadvantage that, firstly a free combination of UV-A and UV-B filters in the cosmetic preparation is no longer possible, and that difficulties in the chemical linkage of the chromophores allow only certain combinations.

U.S. Pat. No. 4,950,467 describes the use of 2,4-pentadienoic acid derivatives as UV absorbers in cosmetic products. The monoaryl-substituted compounds which are mentioned as preferred in this patent likewise have the disadvantage that their photostability is insufficient.

It is an object of the present invention to propose sunscreens for cosmetic and pharmaceutical purposes which absorb in the UV-A region with high extinction, are photostable, have a slight intrinsic color, i.e. a sharp band structure, and are readily soluble in water or in water-miscible solvents.

This object is achieved according to the invention by use of 4,4-diarylbutadienes of the formula I

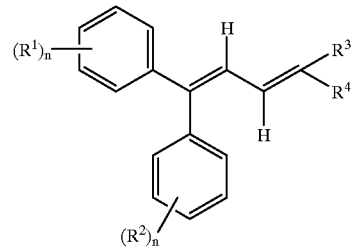

where the diene system has the Z,Z; Z,E; E,Z or E,E configuration or a mixture thereof, and where the variables independently of one another have the following meanings:

$R^1$ and $R^2$ hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted substituents which confer solubility in water and are selected from the group consisting of carboxylate, sulfonate or ammonium radicals;

$R^3$ hydrogen, $COOR^5$, $COR^5$, $CONR^5R^6$, $CN$;

$R^4$ $COOR^6$, $COR^6$, $CONR^5R^6$;

$R^5$ hydrogen, $[X]_o$-$R^7$, $C_1$–$C_6$-alkylene-$SO_3Y$, $C_1$–$C_6$-alkylene-$PO_3Y$, $C_1$–$C_6$-alkylene-$N(R^8)_3{}^+A^-$;

$R^6$ $[X]_o$-$R^7$, $C_1$–$C_6$-alkylene-$SO_3Y$, $C_1$–$C_6$-alkylene-$PO_3Y$, $C_1$–$C_6$-alkylene-$N(R^8)_3{}^{+A^-}$;

X —$CH_2$—$CH_2$—Z—, —$CH_2$—$CH_2$—$CH_2$—Z—, —$CH(CH_3)$—$CH_2$—Z—, —$CH_2$—$CH_2$—$CH_2$—$CH_2$—Z—, —$CH_2$—$CH(CH_2$—$CH_3)$—Z—;

A Cl, Br, I, $SO_4R^9$;

Y hydrogen, $Na^+$, $K^+$, $Mg^{2+}$, $Ca^{2+}$, $Li^+$, $Al^{3+}$, $N(R^8)_4{}^+$;

Z O, NH;

$R^7$ and $R^8$ hydrogen, $C_1$–$C_6$-alkyl, $C_2$–$C_6$-alkenyl, $C_1$–$C_6$-acyl;

$R^9$ hydrogen, $C_1$–$C_6$-alkyl, $C_2$–$C_6$-alkenyl;

n 1 to 3;

1 to 150 as water-soluble photostable UV filters in cosmetic and pharmaceutical preparations for protecting the human skin or human hair from the sun's rays, alone or together with compounds which absorb in the UV region and are known per se for cosmetic and pharmaceutical preparations.

Alkyl radicals $R^1$ and $R^2$ which may be mentioned are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals $R^1$ and $R^2$ which may be mentioned are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Cycloalkyl radicals which may be mentioned for $R^1$ and $R^2$ are preferably branched or unbranched $C_3$–$C_{10}$-cycloalkyl radicals such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Cycloalkenyl radicals which may be mentioned for $R^1$ and $R^2$ are preferably branched or unbranched $C_3$–$C_{10}$-cycloalkenyl radicals with one or more double bonds such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkenyl and cycloalkyl radicals may be unsubstituted or substituted by one or more, e.g. 1 to 3, radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or contain 1 to 3 heteroatoms such as sulfur, nitrogen, whose free valencies can be saturated by hydrogen or $C_1$–$C_4$-alkyl, or oxygen in the ring.

Suitable alkoxy radicals for $R^1$ and $R^2$ are those having 1 to 12 carbon atoms, preferably having 1 to 8 carbon atoms.

Examples which may be mentioned are:

| | |
|---|---|
| methoxy | ethoxy |
| isopropoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Examples of alkoxycarbonyl radicals for $R^1$ and $R^2$ are esters containing the abovementioned alkoxy radicals or radicals derived from higher alcohols, e.g. having up to 20 carbon atoms, such as iso-$C_{15}$ alcohol.

Suitable mono- or dialkylamino radicals for $R^1$ and $R^2$ are those containing alkyl radicals having 1 to 12 carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl means aromatic rings or ring systems having 6 to 18 carbon atoms in the ring system, for example phenyl or naphthyl, each of which may be unsubstituted or substituted by one or more radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Hetaryl radicals are advantageously simple or fused aromatic ring systems having one or more heteroaromatic 3- to 7-membered rings. Heteroatoms which may be present in the ring or ring system are one or more nitrogen, sulfur and/or oxygen atoms.

Hydrophilic radicals, i.e. those making it possible for the compounds of the formula I to dissolve in water, for $R^1$ and $R^2$ are, for example, carboxyl and sulfoxy radicals and, in particular, their salts with any physiologically tolerated cations, such as the alkali metal salts or such as the trialkylammonium salts, such as tri(hydroxyalkyl)ammonium salts or the 2-methyl-1-propanol-2-ammonium salts. Also suitable are ammonium radicals, especially alkylammonium radicals, with any physiologically tolerated anions.

Alkylene groups for $R^5$ and $R^6$ which carry hydrophilic $SO_3Y$, $PO_3Y$ or $N(R^8)_3^+A^-$ radicals which may be mentioned are branched or unbranched $C_1$–$C_6$-alkylene radicals, preferably methylene, ethylene, n-propylene, 1-methylethylene, n-butylene, 1-methylpropylene, 2-methylpropylene, n-pentylene or n-hexylene.

The radical $[X]_o$-$R^7$ for $R^5$ and $R^6$ is, inter alia, polyalkylene glycols which may comprise from 1 to 150 monomer units, preferably from 1 to 50, particularly preferably from 1 to 30, monomer units. X may be an alkylene glycol monomer unit selected from the group consisting of ethylene glycol, n-propylene glycol, 1-methylethylene glycol, n-butylene glycol and 1-ethylethylene glycol. Preferred monomer units may be ethylene glycol, n-propylene glycol and 1-methylethylene glycol.

The polyalkylene glycols may be terminally alkylated, alkenylated or acylated.

Alkyl radicals for $R^7$ to $R^9$ which may be mentioned are branched or unbranched $C_1$–$C_6$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl.

Alkenyl radicals for $R^7$ to $R^9$ which may be mentioned are branched or unbranched $C_2$–$C_6$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl or 2-hexenyl.

Acyl radicals for $R^7$ and $R^8$ which may be mentioned are $C_1$–$C_6$-acyl radicals, preferably formyl, acetyl, propionyl or n-butyryl.

Also suitable for $[X]_o$-$R^7$ are polyalkylenepolyamines, in particular polyethyleneimines which may likewise comprise 1 to 150 monomer units, preferably 1 to 50, particularly preferably 1 to 30 monomer units.

Preferred compounds of the formula I are those where $R^1$ and $R^2$ are, independently of one another, hydrogen, $C_1$–$C_8$-alkyl, $C_1$–$C_8$-alkoxy, $C_1$–$C_8$-alkylamino, $C_1$–$C_8$-dialkylamino, substituents which confer solubility in water and are selected from the group consisting of carboxylate, sulfonate or ammonium radicals;

$R^3$ is $COOR^5$, $CONR^5R^6$, CN;

$R^4$ is $COOR^6$, $CONR^5R^6$;

$R^5$ is hydrogen, $[X]_o$-$R^7$, $C_1$–$C_6$-alkylene-$SO_3Y$, $C_1$–$C_6$-alkylene-$N(R^8)_3{}^+A^-$;

$R^6$ is $[X]_o$-$R^7$, $C_1$–$C_6$-alkylene-$SO_3Y$, $C_1$–$C_6$-alkylene-$N(R^8)_3{}^+A^-$;

X is —$CH_2$—$CH_2$—O—, —$CH_2$—$CH_2$—$CH_2$—O—, —$CH(CH_3)$—$CH_2$—O—;

A is Cl, Br, I, $SO_4R^9$;

Y is hydrogen, $Na^+$, $K^+$, $Mg^{2+}$, $Ca^{2+}$, $Li^+$, $Al^{3+}$, $N(R^8)_4{}^+$;

$R^7$ and $R^9$ are hydrogen, $C_1$–$C_3$-alkyl;

n is 1 to 3;

o is 1 to 50.

$C_1$–$C_8$-Alkyl radicals which are particularly preferred for $R^1$ and $R^6$ are methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 2-ethylhexyl.

Suitable alkoxy radicals for $R^1$ and $R^2$ are, preferably, those having 1 to 8 carbon atoms, and particularly preferably those having 1 to 4 carbon atoms.

Examples which may be mentioned are:

| | |
|---|---|
| methoxy | ethoxy |
| isopropoxy | n-propoxy |
| n-butoxy | 1-methylpropoxy |
| 2-methylpropoxy | |

Suitable and particularly preferred mono- or dialkylamino radicals for $R^1$ and $R^2$ are methyl, ethyl, n-propyl, n-butyl, 2-methylpropyl, 1,1-dimethylpropyl, 2-ethylhexyl.

Particularly preferred $C_1$–$C_3$-alkyl radicals for $R^7$ to $R^9$ which may be mentioned are methyl, ethyl, n-propyl or isopropyl.

Particularly preferred alkylene groups for $R^5$ and $R^6$, which carry hydrophilic $SO_3Y$, $PO_3Y$ or $N(R^8)_3{}^+A^-$ radicals, which may be mentioned are methylene, ethylene, n-propylene, 1-methylethylene or n-butylene.

The substituents $R^1$ and $R^2$ may each be bonded to the aromatic ring in the ortho, meta and/or para position. In the case of disubstituted aromatic rings (n=2), $R^1$ and $R^2$ can be in the ortho/para or meta/para position. Preferred compounds of the formula I where n=1 are those where $R^1$ is identical to $R^2$ and both radicals are in the para position.

Furthermore, compounds of the formula I (n=1) in which the substituents $R^1$ to $R^4$ are present in the combination given in Table 1 have particular photostable properties:

TABLE 1

| $R^1$ | $R^2$ | Position | $R^3$ | $R^4$ |
|---|---|---|---|---|
| H | H | | H | $COR^6$ |
| H | H | | H | $CONR^5R^6$ |
| H | H | | $COOR^5$ | $COOR^6$ |
| H | H | | $COOR^5$ | $COR^6$ |
| H | H | | $COR^5$ | $COR^6$ |
| H | H | | $CONR^5R^6$ | $COOR^6$ |
| H | H | | $CONR^5R^6$ | $COR^6$ |
| H | H | | $CONR^5R^6$ | $CONR^5R^6$ |
| H | H | | CN | $COR^6$ |
| H | H | | CN | $CONR^5R^6$ |
| $C_1$–$C_8$-Alkoxy | $C_1$–$C_8$-Alkoxy | para | H | $COR^6$ |
| $C_1$–$C_8$-Alkoxy | $C_1$–$C_8$-Alkoxy | ortho | H | $COR^6$ |
| $C_1$–$C_8$-Alkoxy | $C_1$–$C_8$-Alkoxy | meta | H | $COR^6$ |
| $C_1$–$C_8$-Alkoxy | $C_1$–$C_8$-Alkoxy | para | H | $CONR^5R^6$ |
| $C_1$–$C_8$-Alkoxy | $C_1$–$C_8$-Alkoxy | ortho | H | $CONR^5R^6$ |
| $C_1$–$C_8$-Alkoxy | $C_1$–$C_8$-Alkoxy | meta | H | $CONR^5R^6$ |
| $C_1$–$C_8$-Alkoxy | $C_1$–$C_8$-Alkoxy | para | $COOR^5$ | $COOR^6$ |
| $C_1$–$C_8$-Alkoxy | $C_1$–$C_8$-Alkoxy | ortho | $COOR^5$ | $COOR^6$ |
| $C_1$–$C_8$-Alkoxy | $C_1$–$C_8$-Alkoxy | meta | $COOR^5$ | $COOR^6$ |
| $C_1$–$C_8$-Alkoxy | $C_1$–$C_8$-Alkoxy | para | $COOR^5$ | $COR^6$ |
| $C_1$–$C_8$-Alkoxy | $C_1$–$C_8$-Alkoxy | ortho | $COOR^5$ | $COR^6$ |
| $C_1$–$C_8$-Alkoxy | $C_1$–$C_8$-Alkoxy | meta | $COOR^5$ | $COR^6$ |
| $C_1$–$C_8$-Alkoxy | $C_1$–$C_8$-Alkoxy | para | $COR^5$ | $COR^6$ |
| $C_1$–$C_8$-Alkoxy | $C_1$–$C_8$-Alkoxy | ortho | $COR^5$ | $COR^6$ |
| $C_1$–$C_8$-Alkoxy | $C_1$–$C_8$-Alkoxy | meta | $COR^5$ | $COR^6$ |
| $C_1$–$C_8$-Alkoxy | $C_1$–$C_8$-Alkoxy | para | $CONR^5R^6$ | $COOR^6$ |
| $C_1$–$C_8$-Alkoxy | $C_1$–$C_8$-Alkoxy | ortho | $CONR^5R^6$ | $COOR^6$ |
| $C_1$–$C_8$-Alkoxy | $C_1$–$C_8$-Alkoxy | meta | $CONR^5R^6$ | $COOR^6$ |
| $C_1$–$C_8$-Alkoxy | $C_1$–$C_8$-Alkoxy | para | $CONR^5R^6$ | $COR^6$ |
| $C_1$–$C_8$-Alkoxy | $C_1$–$C_8$-Alkoxy | ortho | $CONR^5R^6$ | $COR^6$ |
| $C_1$–$C_8$-Alkoxy | $C_1$–$C_8$-Alkoxy | meta | $CONR^5R^6$ | $COR^6$ |
| $C_1$–$C_8$-Alkoxy | $C_1$–$C_8$-Alkoxy | para | $CONR^5R^6$ | $CONR^5R^6$ |
| $C_1$–$C_8$-Alkoxy | $C_1$–$C_8$-Alkoxy | ortho | $CONR^5R^6$ | $CONR^5R^6$ |
| $C_1$–$C_8$-Alkoxy | $C_1$–$C_8$-Alkoxy | meta | $CONR^5R^6$ | $CONR^5R^6$ |
| $C_1$–$C_8$-Alkoxy | $C_1$–$C_8$-Alkoxy | para | CN | $COR^6$ |
| $C_1$–$C_8$-Alkoxy | $C_1$–$C_8$-Alkoxy | ortho | CN | $COR^6$ |
| $C_1$–$C_8$-Alkoxy | $C_1$–$C_8$-Alkoxy | meta | CN | $COR^6$ |
| $C_1$–$C_8$-Alkoxy | $C_1$–$C_8$-Alkoxy | para | CN | $CONR^5R^6$ |
| $C_1$–$C_8$-Alkoxy | $C_1$–$C_8$-Alkoxy | ortho | CN | $CONR^5R^6$ |
| $C_1$–$C_8$-Alkoxy | $C_1$–$C_8$-Alkoxy | meta | CN | $CONR^5R^6$ |
| $C_1$–$C_{12}$-Alkyl | $C_1$–$C_{12}$-Alkyl | para | H | $COR^6$ |
| $C_1$–$C_{12}$-Alkyl | $C_1$–$C_{12}$-Alkyl | ortho | H | $COR^6$ |
| $C_1$–$C_{12}$-Alkyl | $C_1$–$C_{12}$-Alkyl | meta | H | $COR^6$ |
| $C_1$–$C_{12}$-Alkyl | $C_1$–$C_{12}$-Alkyl | para | H | $CONR^5R^6$ |
| $C_1$–$C_{12}$-Alkyl | $C_1$–$C_{12}$-Alkyl | ortho | H | $CONR^5R^6$ |
| $C_1$–$C_{12}$-Alkyl | $C_1$–$C_{12}$-Alkyl | meta | H | $CONR^5R^6$ |
| $C_1$–$C_{12}$-Alkyl | $C_1$–$C_{12}$-Alkyl | para | $COOR^5$ | $COOR^6$ |
| $C_1$–$C_{12}$-Alkyl | $C_1$–$C_{12}$-Alkyl | ortho | $COOR^5$ | $COOR^6$ |
| $C_1$–$C_{12}$-Alkyl | $C_1$–$C_{12}$-Alkyl | meta | $COOR^5$ | $COOR^6$ |
| $C_1$–$C_{12}$-Alkyl | $C_1$–$C_{12}$-Alkyl | para | $COOR^5$ | $COR^6$ |
| $C_1$–$C_{12}$-Alkyl | $C_1$–$C_{12}$-Alkyl | ortho | $COOR^5$ | $COR^6$ |
| $C_1$–$C_{12}$-Alkyl | $C_1$–$C_{12}$-Alkyl | meta | $COOR^5$ | $COR^6$ |
| $C_1$–$C_{12}$-Alkyl | $C_1$–$C_{12}$-Alkyl | para | $COR^5$ | $COR^6$ |
| $C_1$–$C_{12}$-Alkyl | $C_1$–$C_{12}$-Alkyl | ortho | $COR^5$ | $COR^6$ |
| $C_1$–$C_{12}$-Alkyl | $C_1$–$C_{12}$-Alkyl | meta | $COR^5$ | $COR^6$ |
| $C_1$–$C_{12}$-Alkyl | $C_1$–$C_{12}$-Alkyl | para | $CONR^5R^6$ | $COOR^6$ |
| $C_1$–$C_{12}$-Alkyl | $C_1$–$C_{12}$-Alkyl | ortho | $CONR^5R^6$ | $COOR^6$ |
| $C_1$–$C_{12}$-Alkyl | $C_1$–$C_{12}$-Alkyl | meta | $CONR^5R^6$ | $COOR^6$ |
| $C_1$–$C_{12}$-Alkyl | $C_1$–$C_{12}$-Alkyl | para | $CONR^5R^6$ | $COR^6$ |
| $C_1$–$C_{12}$-Alkyl | $C_1$–$C_{12}$-Alkyl | ortho | $CONR^5R^6$ | $COR^6$ |
| $C_1$–$C_{12}$-Alkyl | $C_1$–$C_{12}$-Alkyl | meta | $CONR^5R^6$ | $COR^6$ |
| $C_1$–$C_{12}$-Alkyl | $C_1$–$C_{12}$-Alkyl | para | $CONR^5R^6$ | $CONR^5R^6$ |
| $C_1$–$C_{12}$-Alkyl | $C_1$–$C_{12}$-Alkyl | ortho | $CONR^5R^6$ | $CONR^5R^6$ |

TABLE 1-continued

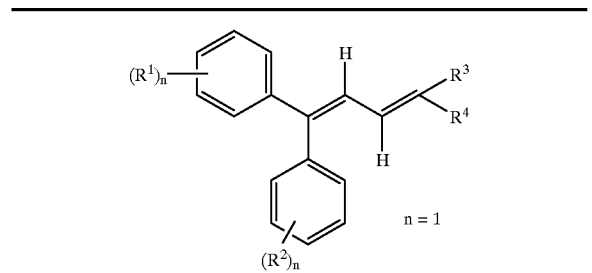

n = 1

| R¹ | R² | Position | R³ | R⁴ |
|---|---|---|---|---|
| $C_1$–$C_{12}$-Alkyl | $C_1$–$C_{12}$-Alkyl | meta | $CONR^5R^6$ | $CONR^5R^6$ |
| $C_1$–$C_{12}$-Alkyl | $C_1$–$C_{12}$-Alkyl | para | CN | $COR^6$ |
| $C_1$–$C_{12}$-Alkyl | $C_1$–$C_{12}$-Alkyl | ortho | CN | $COR^6$ |
| $C_1$–$C_{12}$-Alkyl | $C_1$–$C_{12}$-Alkyl | meta | CN | $COR^6$ |
| $C_1$–$C_{12}$-Alkyl | $C_1$–$C_{12}$-Alkyl | para | CN | $CONR^5R^6$ |
| $C_1$–$C_{12}$-Alkyl | $C_1$–$C_{12}$-Alkyl | ortho | CN | $CONR^5R^6$ |
| $C_1$–$C_{12}$-Alkyl | $C_1$–$C_{12}$-Alkyl | meta | CN | $CONR^5R^6$ |
| Carboxylate | Carboxylate | para | H | $COR^6$ |
| Carboxylate | Carboxylate | ortho | H | $COR^6$ |
| Carboxylate | Carboxylate | meta | H | $COR^6$ |
| Carboxylate | Carboxylate | para | H | $CONR^5R^6$ |
| Carboxylate | Carboxylate | ortho | H | $CONR^5R^6$ |
| Carboxylate | Carboxylate | meta | H | $CONR^5R^6$ |
| Carboxylate | Carboxylate | para | $COOR^5$ | $COOR^6$ |
| Carboxylate | Carboxylate | ortho | $COOR^5$ | $COOR^6$ |
| Carboxylate | Carboxylate | meta | $COOR^5$ | $COOR^6$ |
| Carboxylate | Carboxylate | para | $COOR^5$ | $COR^6$ |
| Carboxylate | Carboxylate | ortho | $COOR^5$ | $COR^6$ |
| Carboxylate | Carboxylate | meta | $COOR^5$ | $COR^6$ |
| Carboxylate | Carboxylate | para | $COR^5$ | $COR^6$ |
| Carboxylate | Carboxylate | ortho | $COR^5$ | $COR^6$ |
| Carboxylate | Carboxylate | meta | $COR^5$ | $COR^6$ |
| Carboxylate | Carboxylate | para | $CONR^5R^6$ | $COOR^6$ |
| Carboxylate | Carboxylate | ortho | $CONR^5R^6$ | $COOR^6$ |
| Carboxylate | Carboxylate | meta | $CONR^5R^6$ | $COOR^6$ |
| Carboxylate | Carboxylate | para | $CONR^5R^6$ | $COR^6$ |
| Carboxylate | Carboxylate | ortho | $CONR^5R^6$ | $COR^6$ |
| Carboxylate | Carboxylate | meta | $CONR^5R^6$ | $COR^6$ |
| Carboxylate | Carboxylate | para | $CONR^5R^6$ | $CONR^5R^6$ |
| Carboxylate | Carboxylate | ortho | $CONR^5R^6$ | $CONR^5R^6$ |
| Carboxylate | Carboxylate | meta | $CONR^5R^6$ | $CONR^5R^6$ |
| Carboxylate | Carboxylate | para | CN | $COR^6$ |
| Carboxylate | Carboxylate | ortho | CN | $COR^6$ |
| Carboxylate | Carboxylate | meta | CN | $COR^6$ |
| Carboxylate | Carboxylate | para | CN | $CONR^5R^6$ |
| Carboxylate | Carboxylate | ortho | CN | $CONR^5R^6$ |
| Carboxylate | Carboxylate | meta | CN | $CONR^5R^6$ |
| Sulfonate | Sulfonate | para | H | $COR^6$ |
| Sulfonate | Sulfonate | ortho | H | $COR^6$ |
| Sulfonate | Sulfonate | meta | H | $COR^6$ |
| Sulfonate | Sulfonate | para | H | $CONR^5R^6$ |
| Sulfonate | Sulfonate | ortho | H | $CONR^5R^6$ |
| Sulfonate | Sulfonate | meta | H | $CONR^5R^6$ |
| Sulfonate | Sulfonate | para | $COOR^5$ | $COOR^6$ |
| Sulfonate | Sulfonate | ortho | $COOR^5$ | $COOR^6$ |
| Sulfonate | Sulfonate | meta | $COOR^5$ | $COOR^6$ |
| Sulfonate | Sulfonate | para | $COOR^5$ | $COR^6$ |
| Sulfonate | Sulfonate | ortho | $COOR^5$ | $COR^6$ |
| Sulfonate | Sulfonate | meta | $COOR^5$ | $COR^6$ |
| Sulfonate | Sulfonate | para | $COR^5$ | $COR^6$ |
| Sulfonate | Sulfonate | ortho | $COR^5$ | $COR^6$ |
| Sulfonate | Sulfonate | meta | $COR^5$ | $COR^6$ |
| Sulfonate | Sulfonate | para | $CONR^5R^6$ | $COOR^6$ |
| Sulfonate | Sulfonate | ortho | $CONR^5R^6$ | $COOR^6$ |
| Sulfonate | Sulfonate | meta | $CONR^5R^6$ | $COOR^6$ |
| Sulfonate | Sulfonate | para | $CONR^5R^6$ | $COR^6$ |
| Sulfonate | Sulfonate | ortho | $CONR^5R^6$ | $COR^6$ |
| Sulfonate | Sulfonate | meta | $CONR^5R^6$ | $COR^6$ |
| Sulfonate | Sulfonate | para | $CONR^5R^6$ | $CONR^5R^6$ |
| Sulfonate | Sulfonate | ortho | $CONR^5R^6$ | $CONR^5R^6$ |
| Sulfonate | Sulfonate | meta | $CONR^5R^6$ | $CONR^5R^6$ |
| Sulfonate | Sulfonate | para | CN | $COR^6$ |
| Sulfonate | Sulfonate | ortho | CN | $COR^6$ |

TABLE 1-continued

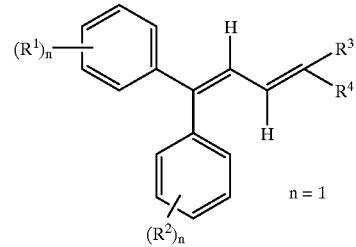

n = 1

| R¹ | R² | Position | R³ | R⁴ |
|---|---|---|---|---|
| Sulfonate | Sulfonate | meta | CN | $COR^6$ |
| Sulfonate | Sulfonate | para | CN | $CONR^5R^6$ |
| Sulfonate | Sulfonate | ortho | CN | $CONR^5R^6$ |
| Sulfonate | Sulfonate | meta | CN | $CONR^5R^6$ |
| Ammonium | Ammonium | para | H | $COR^6$ |
| Ammonium | Ammonium | ortho | H | $COR^6$ |
| Ammonium | Ammonium | meta | H | $COR^6$ |
| Ammonium | Ammonium | para | H | $CONR^5R^6$ |
| Ammonium | Ammonium | ortho | H | $CONR^5R^6$ |
| Ammonium | Ammonium | meta | H | $CONR^5R^6$ |
| Ammonium | Ammonium | para | $COOR^5$ | $COOR^6$ |
| Ammonium | Ammonium | ortho | $COOR^5$ | $COOR^6$ |
| Ammonium | Ammonium | meta | $COOR^5$ | $COOR^6$ |
| Ammonium | Ammonium | para | $COOR^5$ | $COR^6$ |
| Ammonium | Ammonium | ortho | $COOR^5$ | $COR^6$ |
| Ammonium | Ammonium | meta | $COOR^5$ | $COR^6$ |
| Ammonium | Ammonium | para | $COR^5$ | $COR^6$ |
| Ammonium | Ammonium | ortho | $COR^5$ | $COR^6$ |
| Ammonium | Ammonium | meta | $COR^5$ | $COR^6$ |
| Ammonium | Ammonium | para | $CONR^5R^6$ | $COOR^6$ |
| Ammonium | Ammonium | ortho | $CONR^5R^6$ | $COOR^6$ |
| Ammonium | Ammonium | meta | $CONR^5R^6$ | $COOR^6$ |
| Ammonium | Ammonium | para | $CONR^5R^6$ | $COR^6$ |
| Ammonium | Ammonium | ortho | $CONR^5R^6$ | $COR^6$ |
| Ammonium | Ammonium | meta | $CONR^5R^6$ | $COR^6$ |
| Ammonium | Ammonium | para | $CONR^5R^6$ | $CONR^5R^6$ |
| Ammonium | Ammonium | ortho | $CONR^5R^6$ | $CONR^5R^6$ |
| Ammonium | Ammonium | meta | $CONR^5R^6$ | $CONR^5R^6$ |
| Ammonium | Ammonium | para | CN | $COR^6$ |
| Ammonium | Ammonium | ortho | CN | $COR^6$ |
| Ammonium | Ammonium | meta | CN | $COR^6$ |
| Ammonium | Ammonium | para | CN | $CONR^5R^6$ |
| Ammonium | Ammonium | ortho | CN | $CONR^5R^6$ |
| Ammonium | Ammonium | meta | CN | $CONR^5R^6$ |

The invention also relates to 4,4-diarylbutadienes of the formula I, $$\text{I}$$

where the diene system has the Z,Z; Z,E; E,Z or E,E configuration or a mixture thereof, and where the variables independently of one another have the following meanings:

$R^1$ and $R^2$ hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted substituents which confer solubility in water and are selected from the group consisting of carboxylate, sulfonate or ammonium radicals;

$R^3$ hydrogen, $COOR^5$, $COR^5$, $CONR^5R^6$, $CN$;

$R^4$ $COOR^6$, $COR^6$, $CONR^5R^6$;

$R^5$ hydrogen, $[X]_o-R^7$, $C_1-C_6$-alkylene-$SO_3Y$, $C_1-C_6$-alkylene-$PO_3Y$, $C_1-C_6$-alkylene-$N(R^8)_3{}^+A^-$;

$R^6$ $[X]_o-R^7$, $C_1-C_6$-alkylene-$SO_3Y$, $C_1-C_6$-alkylene-$PO_3Y$, $C_1-C_6$-alkylene-$N(R^8)_3{}^+A^-$;

X —$CH_2$—$CH_2$—Z—, —$CH_2$—$CH_2$—$CH_2$—Z—, —$CH(CH_3)$—$CH_2$—Z—, —$CH_2$—$CH_2$—$CH_2$—$CH_2$—Z—, —$CH_2$—$CH(CH_2$—$CH_3)$—Z—;

A Cl, Br, I, $SO_4R^9$;

Y hydrogen, $Na^+$, $K^+$, $Mg^{2+}$, $Ca^{2+}$, $Li^+$, $Al^{3+}$, $N(R^8)_4{}^+$;

Z O, NH;

$R^7$ and $R^8$ hydrogen, $C_1-C_6$-alkyl, $C_2-C_6$-alkenyl, $C_1-C_6$-acyl;

$R^9$ hydrogen, $C_1-C_6$-alkyl, $C_2-C_6$-alkenyl;

n 1 to 3;

o 1 to 150.

Preference is given to 4,4-diarylbutadienes of the formula Ia,

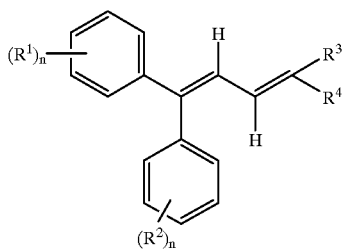

where the diene system has the Z,Z; Z,E; E,Z or E,E configuration or a mixture thereof, and where the variables independently of one another have the following meanings:

$R^1$ and $R^2$ hydrogen, $C_1-C_8$-alkyl, $C_1-C_8$-alkoxy, substituents which confer solubility in water and are selected from the group consisting of carboxylate, sulfonate or ammonium radicals;

$R^3$ $COOR^5$, $CONR^5R^6$, $CN$;

$R^4$ $COOR^6$, $CONR^5R^6$;

$R^5$ hydrogen, $[X]_o-R^7$, $C_1-C_6$-alkylene-$SO_3Y$, $C_1-C_6$-alkylene-$N(R^8)_3{}^+A^-$;

$R^6$ $[X]_o-R^7$, $C_1-C_6$-alkylene-$SO_3Y$, $C_1-C_6$-alkylene-N$(R^8)_3{}^+A^-$;

X —$CH_2$—$CH_2$—O—, —$CH_2$—$CH_2$—$CH_2$—O—, —$CH(CH_3)$—$CH_2$—O—;

A Cl, Br, I, $SO_4R^9$;

Y hydrogen, $Na^+$, $K^+$, $Mg^{2+}$, $Ca^{2+}$, $Li^+$, $Al^{3+}$, $N(R^8)_4{}^+$;

$R^7$ to $R^9$ hydrogen, $C_1-C_3$-alkyl;

n 1 to 3;

o 1 to 50.

Particular preference is given to 4,4-diarylbutadienes of the formula Ib,

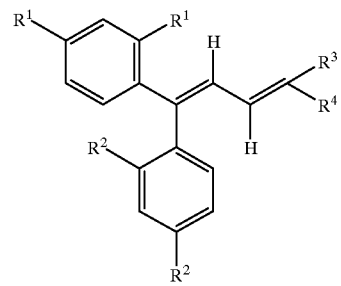

where the diene system has the Z,Z; Z,E; E,Z or E,E configuration or a mixture thereof, and where the variables independently of one another have the following meanings:

$R^1$ and $R^2$ hydrogen, $C_1-C_8$-alkyl, $C_1-C_8$-alkoxy;

$R^3$ $COOR^5$, $CONR^5R^6$, $CN$;

$R^4$ $COOR^6$, $CONR^5R^6$;

$R^5$ hydrogen, $[X]_o-R^7$, $C_1-C_6$-alkylene-$SO_3Y$, $C_1-C_6$-alkylene-$N(R^8)_3{}^+A^-$;

$R^6$ $[X]_o-R^7$, $C_1-C_6$-alkylene-$SO_3Y$, $C_1-C_6$-alkylene-N$(R^8)_3{}^+A^-$;

X —$CH_2$—$CH_2$—O—, —$CH_2$—$CH_2$—$CH_2$—O—, —$CH(CH_3)$—$CH_2$—O—;

A Cl, Br, I, $SO_4R^9$;

Y hydrogen, $Na^+$, $K^+$, $Mg^{2+}$, $Ca^{2+}$, $Li^+$, $Al^{3+}$, $N(R^8)_4{}^+$;

$R^7$ to $R^9$ hydrogen, $C_1-C_3$-alkyl;

o 1 to 50.

Very particular preference is given to 4,4-diarylbutadienes of the formula Ic,

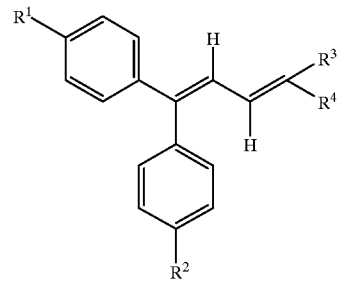

where the diene system has the Z,Z; Z,E; E,Z or E,E configuration or a mixture thereof, and where the variables independently of one another have the following meanings:

$R^1$ and $R^2$ hydrogen, $C_1-C_8$-alkyl, $C_1-C_8$-alkoxy;

$R^3$ $COOR^5$, $CONR^5R^6$, $CN$;

$R^4$ $COOR^6$, $CONR^5R^6$;

$R^5$ hydrogen, $[X]_o-R^7$, $C_1-C_6$-alkylene-$SO_3Y$, $C_1-C_6$-alkylene-$N(R^8)_3{}^+A^-$;

$R^6$ $[X]_o-R^7$, $C_1-C_6$-alkylene-$SO_3Y$, $C_1-C_6$-alkylene-N$(R^8)_3{}^+A^-$;

X —$CH_2$—$CH_2$—O—, —$CH_2$—$CH_2$—$CH_2$—O—, —$CH(CH_3)$—$CH_2$—O—;

A Cl, Br, I, $SO_4R^9$;

Y hydrogen, $Na^+$, $K^+$, $Mg^{2+}$, $Ca^{2+}$, $Li^+$, $Al^{3+}$, $N(R^8)_4{}^+$;

$R^7$ to $R^9$ hydrogen, $C_1-C_3$-alkyl;

o 1 to 50.

The more accurate definition of the substituents $R^1$ to $R^9$ of the compounds I and the preferred representatives Ia to Ic corresponds to the description of the compound I already given in the introduction.

The compounds of the formula I to be used according to the invention can be prepared by condensation in accordance with the equation

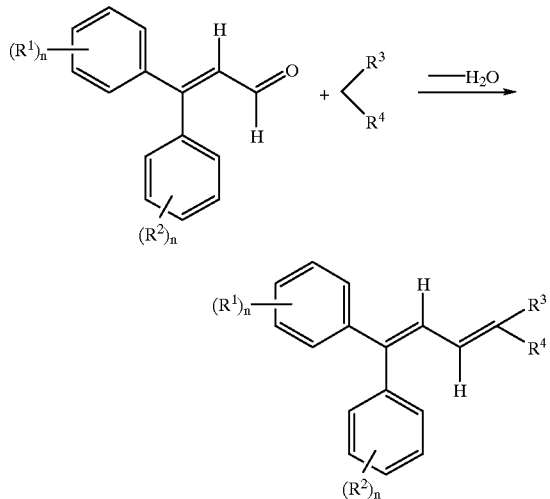

where $R^1$ to $R^4$ have the meanings stated in claim 1.

The abovementioned condensation can be either base- or acid-catalyzed. Suitable catalysts are:

tertiary amines such as, for example, pyridine, morpholine, triethylamine, triethanolamine;

seconday amines such as, for example, piperidine, dimethylamine, diethylamine;

$NH_3$, $NaNH_2$, $KNH_2$, $NH_4OAc$;

basic alumina, basic ion exchangers;

$Na_2CO_3$, $K_2CO_3$;

acid catalysts such as, for example, glacial acetic acid, formic acid, propionic acid;

HCl, $H_2SO_4$, $HNO_3$;

acid ion exchangers.

The amount of the catalysts is generally from 0.1 to 50 mol %, preferably 0.5 to 20 mol %, of the amount of aldehyde employed.

The temperatures preferably employed are from 20 to 150° C., in particular 30 to 100° C., particularly preferably 40 to 80° C. No special conditions regarding the pressure are necessary; the reaction is generally carried out under atmospheric pressure.

Solvents which can be employed are alcohols such as, for example, methanol, ethanol or isopropanol; aromatic compounds such as, for example, toluene or xylene; hydrocarbons, for example heptane or hexane; chlorinated hydrocarbons such as, for example, chloroform or dichloromethane; miglyol, tetrahydrofuran. However, the reaction can also be carried out without solvent.

It is also possible to prepare longer-chain esters starting from methyl or ethyl esters such as, for example, compound 1 in Table 2, by transesterification reactions in the presence of a basic catalyst.

Catalysts suitable for the transesterification are:

basic alkali metal and alkaline earth metal salts, preferably those which are soluble neither in the starting materials nor in the products and which can easily be removed after the end of the reaction, particularly preferably: sodium, potassium or calcium carbonate or sodium hydrogencarbonate;

alkaline earth metal oxides, preferably calcium or magnesium oxide and basic zeolites.

The amount of the catalysts is generally from 1 to 80 mol %, preferably 5 to 50 mol %, of the amount of ester employed.

The amount of alcohol employed must be at least equimolar to the amount of starting ester employed, for example compound 1 in Table 2. Amounts of from 200 to 500 mol % of the alcohol are preferably used.

The methanol or ethanol which is formed is removed by distillation.

The temperatures preferably employed are from 50 to 250° C., in particular 60 to 150° C. No special conditions regarding the pressure are necessary; the reaction is generally carried out under atmospheric pressure.

Solvents which can be employed are inert, high-boiling compounds such as xylenes, but also toluene or mixtures of the alcohols employed with liquid, short-chain alkanes such as hexane and heptane. It is preferred to use no solvent in the alcohol employed.

The transesterification can be carried out either batchwise or continuously. In the continuous procedure, the reactants are preferably passed over a fixed bed of an insoluble base.

In the case where $R^3 \neq R^4$, the compounds of the formula I according to the invention can, in principle, be in the form of their various geometric isomers, i.e. with a diene system having the Z,Z; Z,E; E,Z and/or E,E configuration. The preferred cosmetic sunscreens are the all-E and/or all-Z isomers, very particularly preferably the all-E isomers.

If $R^3 = R^4$, the C—C double bond between C-3 and C-4 (adjacent to the diaryl system) can have the E and/or Z configuration, preferably the Z configuration.

The present invention also relates to cosmetic and pharmaceutical preparations which comprise from 0.1 to 10% by weight, preferably 1 to 7% by weight, based on the total amount of the cosmetic and pharmaceutical preparation, of one or more of the compounds of the formula I together with compounds which absorb in the UV-A and UV-B regions and are known per se for cosmetic and pharmaceutical preparations as sunscreens, where the compounds of the formula I are generally employed in a smaller amount than the UV-B-absorbing compounds.

The sunscreen-containing cosmetic and pharmaceutical preparations are, as a rule, based on a carrier which contains at least one oil phase. However, preparations with an exclusively aqueous basis are also possible on use of compounds having hydrophilic substituents. Accordingly, oils, oil-in-water and water-in-oil emulsions, creams and pastes, protective lipstick compositions or non-greasy gels are suitable.

Sunscreen products of these types can accordingly be in liquid, paste or solid form, for example as water-in-oil creams, oil-in-water creams and lotions, aerosol foam creams, gels, oils, wax pencils, powders, sprays or alcoholic-aqueous lotions.

The compounds of the formula I according to the invention can advantageously be incorporated into the aqueous or alcoholic-aqueous phase for preparation of the abovementioned sunscreens.

Examples of conventional cosmetic oil components are paraffin oil, glyceryl stearate, isopropyl myristate, diisopropyl adipate, cetylstearyl 2-ethylhexanoate, hydrogenated polyisobutene, petrolatum, caprylic acid/capric acid triglycerides, microcrystalline wax, lanolin and stearic acid.

Conventional cosmetic ancillary substances which may be suitable as additives are, for example, coemulsifiers, fats and waxes, stabilizers, thickeners, biogenic active substances, film formers, fragrances, dyes, pearlizing agents, preservatives, pigments, electrolytes (e.g. magnesium sulfate) and pH regulators. Suitable and preferred coemulsifiers are known W/O as well as O/W emulsifiers such as polyglycerol esters, sorbitan esters or partially esterified glycerides. Typical examples of fats are glycerides; waxes which may be mentioned are, inter alia, beeswax, paraffin wax or microwaxes, possibly combined with hydrophilic waxes. Stabilizers which can be employed are metal salts of fatty acids such as, for example, magnesium, aluminum and/or zinc stearate. Examples of suitable thickeners are crosslinked polyacrylic acids and their derivatives, polysaccharides, in particular xanthan gum, guar-guar, agar-agar, alginates and tyloses, carboxymethylcellulose and hydroxyethylcellulose, also fatty alcohols, monoglycerides and fatty acids, polyacrylates, polyvinyl alcohol and polyvinylpyrrolidone. Examples of biogenic active substances are plant extracts, protein hydrolysates and vitamin complexes. Examples of film formers which are in use are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlizing agents are glycol distearic esters such as ethylene glycol distearate, but also fatty acids and fatty acid monoglycol esters. Dyes which can be used are the substances suitable and approved for cosmetic purposes, as tabulated, for example, in the publication "Kosmetische Färbemittel" of the Farbstoffkommission der Deutschen Forschungsgemeinschaft, published by Verlag Chemie, Weinheim, 1984. These dyes are normally employed in a concentration of from 0.001 to 0.1% of the total weight of the mixture.

The total content of ancillary substances and additives can be from 1 to 80, preferably 6 to 40, % by weight, and the nonaqueous content ("active substance") can be from 20 to 80, preferably 30 to 70, % by weight, based on the compositions. The compositions can be produced in a manner known per se, i.e. for example by hot, cold, hot-hot/cold or PIT emulsification. This is a purely mechanical process; no chemical reaction takes place.

Finally, it is also possible to use other substances which absorb in the UV region and are known per se as long as they are stable in the complete system of the combination of UV filters to be used according to the invention.

Most of the sunscreens in the cosmetic and pharmaceutical preparations used for protecting the human epidermis consist of compounds which absorb UV light in the UV-B region, i.e. in the region from 280 to 320 nm. The content of UV-A absorbers to be used according to the invention is, for example, from 10 to 90%, preferably 20 to 50%, of the total weight of UV-B- and UV-A-absorbing substances.

Any UV-A and UV-B filter substances are suitable as UV filter substances which are used in combination with the compounds of the formula I to be used according to the invention. Examples which may be mentioned are:

TABLE 2

| No. | Substance | CAS No. (= acid) |
|---|---|---|
| 1 | 4-Aminobenzoic acid | 150-13-0 |
| 2 | 3-(Trimethylammonio)benzylidenebornan-2-one methyl sulfate | 52793-97-2 |

TABLE 2-continued

| No. | Substance | CAS No. (= acid) |
|---|---|---|
| 3 | 3,3,5-Trimethylcyclohexyl salicylate (homosalate) | 118-56-9 |
| 4 | 2-Hydroxy-4-methoxybenxophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methane-sulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Methylbenzylidene)bornan-2-one | 36861-47-9 |
| 14 | 3-Benzylidenebornan-2-one | 15087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Tri(o-2-ethylhexoxycarbonyl-anilino)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2-Ethylhexyl 2-cyano-3,3-diphenylacrylate | 6197-30-4 |
| 21 | Menthyl o-aminobenzoate or: 5-methyl-2-(1-methylethyl)cyclohexyl 2-aminobenzoate | 134-09-8 |
| 22 | Glyceryl p-aminobenzoate or: 4-aminobenzoic acid 1-glyceryl ester | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-1 |
| 27 | 3-(4'-Sulfobenzylidene)bornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |

Finally, mention may also be made of micronized pigments such as titanium dioxide and zinc oxide.

To protect human hair from UV rays, the sunscreens of the formula I according to the invention can be incorporated into shampoos, lotions, gels, hair sprays, aerosol foam creams or emulsions in concentrations of from 0.1 to 10% by weight, preferably 1 to 7% by weight. The particular formulations can be used inter alia for washing, coloring and styling the hair.

Compounds of the formula I which are particularly preferred for this purpose are those in which the substituents $R^3$ and/or $R^4$ are cationic radicals, such as, for example, compound 2 in Table 3.

The compounds to be used according to the invention as a rule have a particularly high absorbance in the region of UV-A radiation with a sharp band structure. They are furthermore readily soluble in aqueous or alcoholic-aqueous systems and can thus easily be incorporated into the aqueous phase of cosmetic formulations. The emulsions prepared using the compounds I show particularly high stability, the compounds I themselves show high photostability, and the preparations produced with I have a pleasant feel on the skin.

The UV filter action of the compounds of the formula I according to the invention can also be utilized for stabilizing active and ancillary substances in cosmetic and pharmaceutical formulations.

The invention also relates to the compounds of the formula I for use as a medicament and to pharmaceutical compositions for the preventive treatment of inflammation and allergies of the skin, and for preventing certain types of skin cancer, which comprise an effective amount of at least one compound of the formula I as active substance.

The pharmaceutical composition according to the invention can be administered orally or topically. For oral administration, the pharmaceutical composition is in the form of, inter alia, pastilles, gelatine capsules, coated tablets, as a syrup, solution, emulsion or suspension. The pharmaceutical compositions are used topically for example as an ointment, cream, gel, spray, solution or lotion.

EXAMPLES

I. PREPARATION

Example 1

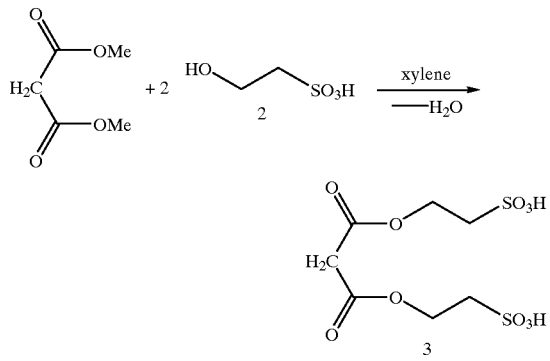

0.1 mol of dimethyl malonate (1) was heated with 0.2 mol of 2-hydroxyethylsulfonic acid (2) in xylene. The water of reaction was continuously removed azeotropically. After all of the water of reaction had been removed, the organic phase was washed with 2 n NaOH, and the desired product (3) was crystallized from the aqueous phase by acidification with $H_2SO_4$ to pH=2. Yield: 75% of theory.

Example 2

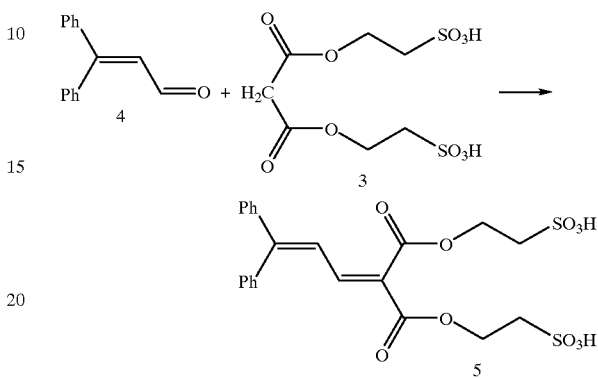

0.11 mol of compound 3 from Example 1 was added to 0.1 mol of β-phenylcinnamaldehyde (4) in 100 ml of xylene. After 0.01 mol of piperidine had been added, the reaction mixture was refluxed for 4 h. The mixture was then cooled and washed with 2 n NaOH, and the aqueous phase, following phase separation, was adjusted to pH=2, during which the product (5) precipitated out. Yield: 82% of theory. Purity: >98% (HPLC). $E^1_1$=650, $\lambda_{max}$=336 nm.

The compounds listed in Table 3 were prepared as in Example 2.

TABLE 3

| No. | | $E^1_1$ | $\lambda_{max}$ |
|---|---|---|---|
| 1 | Ph₂C=CH–CH=C(CN)–C(O)–O–CH₂CH₂–S(O)₂–OH | 680 | 354 |
| 2 | Ph₂C=CH–CH=C[C(O)NH–(CH₂)₃–N⁺(CH₃)₂–OS(O)₂OMe]₂ | 450 | 330 |

TABLE 3-continued

| No. | | $E^1_1$ | $\lambda_{max}$ |
|---|---|---|---|
| 3 | Ph-CH=CH-C(=C(COO-CH2CH2-O-CH2CH2-O-CH2CH2-OCH3)(COO-CH2CH2-O-CH2CH2-OCH3)) with Ph2C= | 600 | 335 |

The compounds in Tables 4 and 5 can be prepared as in Example 2 or as described in the general section.

TABLE 4

[Structure: (R¹)ₙ-phenyl-C(=CH-C(COOR⁵)(COOR⁶))-phenyl-(R²)ₙ with H's shown; R⁵ = R⁶]

| No. | R⁵ = R⁶ | R¹ | R² | n | Position |
|---|---|---|---|---|---|
| 1) | —(CH₂)₂—SO₃Na | H | H | 1 | — |
| 2) | —(CH₂)₃—SO₃Na | H | H | 1 | — |
| 3) | —(CH₂)₂—SO₃Na | CH₃ | CH₃ | 1 | para |
| 4) | —(CH₂)₃—SO₃Na | CH₃ | CH₃ | 1 | para |
| 5) | [—(CH₂)₂—O—]₃—CH₃ | CH₃ | CH₃ | 1 | para |
| 6) | —(CH₂)₂—SO₃Na | CH₃O | CH₃O | 1 | para |
| 7) | —(CH₂)₃—SO₃Na | CH₃O | CH₃O | 1 | para |
| 8) | [—(CH₂)₂—O—]₃—CH₃ | CH₃O | CH₃O | 1 | para |
| 9) | —(CH₂)₂—SO₃Na | SO₃Na | SO₃Na | 1 | para |
| 10) | —(CH₂)₃—SO₃Na | SO₃Na | SO₃Na | 1 | para |
| 11) | [—(CH₂)₂—O—]₃—CH₃ | SO₃Na | SO₃Na | 1 | para |
| 12) | —(CH₂)₂—SO₃Na | COONa | COONa | 1 | para |
| 13) | —(CH₂)₃—SO₃Na | COONa | COONa | 1 | para |
| 14) | [—(CH₂)₂—O—]₃—CH₃ | COONa | COONa | 1 | para |

TABLE 5

[Structure: (R¹)ₙ-phenyl-C(=CH-C(COOR⁵R⁶)(COOR⁵R⁶))-phenyl-(R²)ₙ; R⁵ ≠ R⁶]

| No. | R⁵ | R⁶ | R¹ | R² | n | Position |
|---|---|---|---|---|---|---|
| 1) | H | —(CH₂)₃—N(CH₃)₃⁺Cl⁻ | H | H | 1 | — |
| 2) | H | [—(CH₂)₂—O—]₃—CH₃ | H | H | 1 | — |
| 3) | H | [—(CH₂)₂—O—]₄—CH₃ | H | H | 1 | — |

TABLE 5-continued

| No. | R⁵ | R⁶ | R¹ | R² | n | Position |
|---|---|---|---|---|---|---|
| 4) | H | [—(CH₂)₂—O—]₅—CH₃ | H | H | 1 | — |
| 5) | H | —(CH₂)₃—N(CH₃)₃⁺Cl⁻ | CH₃ | CH₃ | 1 | para |
| 6) | H | [—(CH₂)₂—O—]₃—CH₃ | CH₃ | CH₃ | 1 | para |
| 7) | H | [—(CH₂)₂—O—]₄—CH₃ | CH₃ | CH₃ | 1 | para |
| 8) | H | [—(CH₂)₂—O—]₅—CH₃ | CH₃ | CH₃ | 1 | para |
| 9) | H | —(CH₂)₃—N(CH₃)₃⁺Cl⁻ | CH₃O | CH₃O | 1 | para |
| 10) | H | [—(CH₂)₂—O—]₃—CH₃ | CH₃O | CH₃O | 1 | para |
| 11) | H | [—(CH₂)₂—O—]₄—CH₃ | CH₃O | CH₃O | 1 | para |
| 12) | H | [—(CH₂)₂—O—]₅—CH₃ | CH₃O | CH₃O | 1 | para |
| 13) | H | —(CH₂)₃—N(CH₃)₃⁺Cl⁻ | SO₃Na | SO₃Na | 1 | para |
| 14) | H | [—(CH₂)₂—O—]₃—CH₃ | SO₃Na | SO₃Na | 1 | para |
| 15) | H | [—(CH₂)₂—O—]₄—CH₃ | SO₃Na | SO₃Na | 1 | para |
| 16) | H | [—(CH₂)₂—O—]₅—CH₃ | SO₃Na | SO₃Na | 1 | para |
| 17) | H | —(CH₂)₃—N(CH₃)₃⁺Cl⁻ | COONa | COONa | 1 | para |
| 18) | H | [—(CH₂)₂—O—]₃—CH₃ | COONa | COONa | 1 | para |
| 19) | H | [—(CH₂)₂—O—]₄—CH₃ | COONa | COONa | 1 | para |
| 20) | H | [—(CH₂)₂—O—]₅—CH₃ | COONa | COONa | 1 | para |

Example 4

Standardized Method for Photostability Determination (Suntest)

A 5% by weight alcoholic-aqueous solution of the sunscreen to be tested is applied, using an Eppendorf pipette (20 μl), to the milled area on a small glass plate. Owing to the presence of the alcohol, the solution is distributed uniformly on the roughened glass surface. The amount applied corresponds to the amount of sunscreen required to obtain an average sun protection factor in suncreams. In the test, 4 glass plates are irradiated each time. The evaporation time and the irradiation each last for 30 minutes. The glass plates are cooled slightly during the irradiation by a water cooling system located at the base of the Suntest apparatus. The temperature inside the Suntest apparatus during the irradiation is 40° C. After the samples have been irradiated, they are washed with ethanol into a dark 50 ml graduated flask and measured using a photometer. The blank samples are applied in the same way to glass plates and evaporated at room temperature for 30 minutes. Like the other samples, they are washed off with ethanol and diluted to 100 ml and measured.

Photostability Comparative Tests:

1.

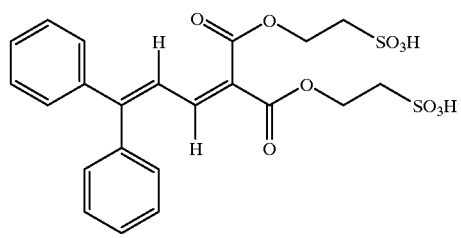

Photostability: 98%

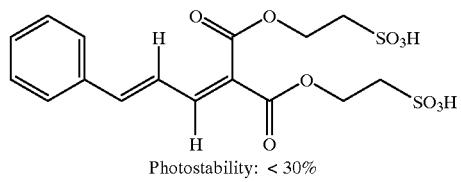

Photostability: < 30%

General Method for Preparing Emulsions for Cosmetic Purposes

All of the oil-soluble ingredients are heated to 85° C. in a stirred vessel. When all the ingredients have melted or are present as liquid phase, the aqueous phase, which comprises, in the dissolved state, the 4,4-diarylbutadienes of the formula I according to the invention, possibly in the form of their salts, is incorporated by homogenization. The emulsion is cooled to about 40° C. with stirring, is perfumed and homogenized, and is then cooled to 25° C. while stirring continuously.

Preparations

Example 5

| Lip care composition Mass content (% by weight) | |
|---|---|
| ad 100 | eucerinum anhydricum |
| 10.00 | glycerol |
| 10.00 | titanium dioxide |
| 5.00 | compound from Example 2 |
| 8.00 | octyl methoxycinnamate |
| 5.00 | zinc oxide |
| 4.00 | castor oil |
| 4.00 | pentaerythrityl stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

Example 6

| Lip care composition Mass content (% by weight) | |
|---|---|
| ad 100 | eucerinum anhydricum |
| 10.00 | glycerol |
| 10.00 | titanium dioxide |
| 5.00 | compound No. 1 in Table 3 |
| 8.00 | octyl methoxycinnamate |
| 5.00 | zinc oxide |
| 4.00 | castor oil |
| 4.00 | pentaerythrityl stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

Example 7

| Sunblocker composition with micropigments Mass content (% by weight) | |
|---|---|
| ad 100 | water |
| 10.00 | octyl methoxycinnamate |
| 6.00 | PEG-7 hydrogenated castor oil |
| 6.00 | titanium dioxide |
| 5.00 | compound from Example 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEC-40 hydrogenated castor oil |
| 0.50 | tocopheryl acetate |
| 0.50 | phenoxyethanol |
| 0.20 | EDTA |

Example 8

| Sunblocker composition with micropigments Mass content (% by weight) | |
|---|---|
| ad 100 | water |
| 10.00 | octyl methoxycinnamate |
| 6.00 | PEG-7 hydrogenated castor oil |
| 6.00 | titanium dioxide |
| 5.00 | compound No. 1 in Table 3 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

Example 9

| | Non-greasy gel Mass content (% by weight) |
|---|---|
| ad 100 | water |
| 8.00 | octyl methoxycinnamate |
| 7.00 | titanium dioxide |
| 5.00 | compound from Example 2 |
| 5.00 | glycerol |
| 5.00 | PEG-25 PABA |
| 1.00 | 4-methylbenzylidenecamphor |
| 0.40 | acrylaze C10—C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

Example 10

| | Non-greasy gel Mass content (% by weight) |
|---|---|
| ad 100 | water |
| 8.00 | octyl methoxycinnamate |
| 7.00 | titanium dioxide |
| 5.00 | compound No. 1 in Table 3 |
| 5.00 | glycerol |
| 5.00 | PEG-25 PABA |
| 1.00 | 4-methylbenzylidenecamphor |
| 0.40 | acrylate C10—C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

Example 11

| | Suncream (SPF 20) Mass content (% by weight) |
|---|---|
| ad 100 | water |
| 8.00 | octyl methoxycinnamate |
| 8.00 | titanium dioxide |
| 6.00 | PEG-7 hydrogenated castor oil |
| 5.00 | compound from Example 2 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

Example 12

| | Suncream (SPF 20) Mass content (% by weight) |
|---|---|
| ad 100 | water |
| 8.00 | octyl methoxycinnamate |
| 8.00 | titanium dioxide |
| 6.00 | PEG-7 hydrogenated castor oil |
| 5.00 | compound No. 1 in Table 3 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | diodium EDTA |
| 0.15 | propylparaben |

Example 13

| | Water-resistant suncream Mass content (% by weight) |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | compound from Example 2 |
| 4.00 | glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |

Example 14

| | Water-resistant suncream Mass content (% by weight) |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | compound No. 1 in Table 3 |
| 4.00 | glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |

Example 15

| Sunmilk (SPF 6) Mass content (% by weight) | |
|---|---|
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 5.00 | compound from Example 2 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |

Example 16

| Sunmilk (SPF 6) Mass content (% by weight) | |
|---|---|
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 5.00 | compound No. 1 in Table 3 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |

We claim:

1. The method of using 4,4-diarylbutadienes of the formula I,

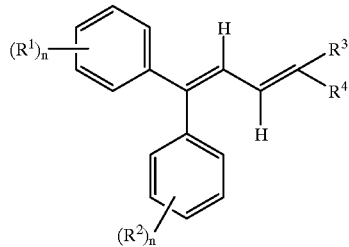

where the diene system has the Z,Z; Z,E; E,Z or E,E configuration or a mixture thereof, and where the variables independently of one another have the following meanings:

$R^1$ and $R^2$ hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted substituents which confer solubility in water and are selected from the group consisting of carboxylate, sulfonate or ammonium radicals;

$R^3$ hydrogen, $COOR^5$, $COR^5$, $CONR^5R^6$, CN;

$R^4$ $COOR^6$, $COR^6$, $CONR^5R^6$;

$R^5$ hydrogen, $[X]_o$-$R^7$, $C_1$–$C_6$-alkylene-$SO_3Y$, $C_1$–$C_6$-alkylene-$PO_3Y$, $C_1$–$C_6$-alkylene-$N(R^8)_3{}^+A^-$;

$R^6$ $[X]_o$-$R^7$, $C_1$–$C_6$-alkylene-$SO_3Y$, $C_1$–$C_6$-alkylene-$PO_3Y$, $C_1$–$C_6$-alkylene-$N(R^8)_3{}^+A^-$;

X —$CH_2$—$CH_2$—Z—, —$CH_2$—$CH_2$—$CH_2$—Z—, —$CH(CH_3)$—$CH_2$—Z—, —$CH_2$—$CH_2$—$CH_2$—$CH_2$—Z—, —$CH_2$—$CH(CH_2$—$CH_3)$—Z—;

A Cl, Br, I, $SO_4R^9$;

Y hydrogen, $Na^+$, $K^+$, $Mg^{2+}$, $Ca^{2+}$, $Li^+$, $Al^{3+}$, $N(R^8)_4{}^+$;

Z O, NH;

$R^7$ and $R^8$ hydrogen, $C_1$–$C_6$-alkyl, $C_2$–$C_6$-alkenyl, $C_1$–$C_6$-acyl;

$R^9$ hydrogen, $C_1$–$C_6$-alkyl, $C_2$–$C_6$-alkenyl;

n 1 to 3;

o 1 to 150 as water-soluble photostable UV filters in cosmetic and pharmaceutical preparations for protecting the human skin or human hair from the sun's rays, alone or together with compounds which absorb in the UV region and are known for cosmetic and pharmaceutical preparations.

2. The method of using compounds of the formula I as claimed in claim 1 as water-soluble photostable UV-A filters.

3. The method of using compounds of the formula I claim 1 as water-soluble UV stabilizers in cosmetic and pharmaceutical formulations.

4. A sunscreen-containing cosmetic or pharmaceutical preparation for protecting the human epidermis or human hair from UV light in the range from 280 to 400 nm, which comprises, in a cosmetically or pharmaceutically suitable carrier, alone or together with compounds which absorb in the UV region and are known per se for cosmetic and pharmaceutical preparations, amounts, which are effective as photostable UV filters, of compounds of the formula I

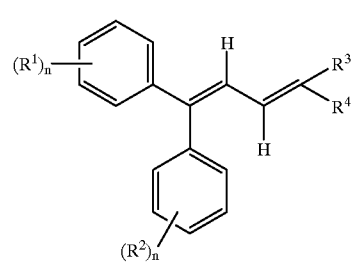

where the variables have the meanings stated in claim 1.

* * * * *